United States Patent [19]

Zoncada

[11] Patent Number: 5,516,049

[45] Date of Patent: May 14, 1996

[54] HOSPITAL REFUSE STERILIZATION PLANT

[75] Inventor: Renato Zoncada, deceased, late of Pavia, Italy, by Stefania Zoncada, Silvana Foletti, heiress

[73] Assignee: Econos S.R.L., Milan, Italy

[21] Appl. No.: 325,518

[22] Filed: Oct. 19, 1994

[30] Foreign Application Priority Data

Oct. 20, 1993 [IT] Italy ............................. MI9300800 U

[51] Int. Cl.⁶ ..................... B02C 21/00; B02C 23/18; A61L 2/12
[52] U.S. Cl. ................... 241/34; 241/41; 241/65; 241/222; 241/224; 241/606; 204/158.21; 219/686; 220/87.1; 422/21; 422/38; 422/119; 422/309; 588/227; 588/258; 588/900
[58] Field of Search .................. 241/34, 41, 65, 241/222, 224, 236, 606, DIG. 38; 204/157.43, 158.2, 158.21; 219/678, 686; 220/87.1; 250/455.11; 378/64; 422/4, 21–23, 26, 38, 105, 119, 291, 307, 309; 423/DIG. 18; 588/210, 211, 212, 227, 258, 900

[56] References Cited

U.S. PATENT DOCUMENTS

| | | | |
|---|---|---|---|
| 2,731,208 | 1/1956 | Dodd | 241/606 X |
| 4,469,043 | 9/1984 | Kohler et al. | 118/63 |
| 4,578,185 | 3/1986 | Wilson et al. | 241/606 X |
| 5,223,231 | 6/1993 | Drake | 422/21 X |
| 5,294,412 | 3/1994 | Orlando | 588/258 X |
| 5,322,603 | 6/1994 | Kamech et al. | 422/21 X |
| 5,346,142 | 9/1994 | Miller et al. | 241/606 X |
| 5,348,235 | 9/1994 | Pappas | 422/21 X |
| 5,362,443 | 11/1994 | Tanaka et al. | 241/606 X |
| 5,393,500 | 2/1995 | Kameda et al. | 422/21 X |

FOREIGN PATENT DOCUMENTS

| | | | |
|---|---|---|---|
| 393231 | 10/1990 | European Pat. Off. | A61L 11/00 |
| 3627367 | 12/1987 | Germany | A61L 11/00 |
| 4128854 | 12/1992 | Germany | A61L 11/00 |
| 2232594 | 12/1990 | United Kingdom | A61L 11/00 |

Primary Examiner—Timothy V. Eley
Attorney, Agent, or Firm—Cushman Darby & Cushman

[57] ABSTRACT

To reliably sterilize hospital refuse in a quantities and configuration in which it occurs on its collection, the plant includes a refuse loading device, a shredder, a motorized screw for refuse conveying, a microwave oven and a device for removing the treated refuse upon its exit from the oven.

15 Claims, 6 Drawing Sheets

HOSPITAL REFUSE STERILIZATION PLANT

BACKGROUND OF THE INVENTION

This invention relates to a hospital refuse sterilization plant. Hospital refuse cannot be disposed of by dumping because of its potential infective power, and has therefore to be disposed of by incineration. However, to prevent the contagion which it could generate during the handling involved in its transport to the incinerator, particular care has to be taken which further increases the already high cost of disposal by incineration. The problems connected with overall safety and cost could be solved if such refuse could be sterilized prior to its disposal. In such a case the refuse could be dumped as normal domestic refuse. However the sterilization of hospital refuse in the quantities and configuration in which it occurs on its collection for feeding to disposal cannot be validly achieved with the hoped-for efficiency, economy and guarantee of sterilization using current equipment, because of the particular nature of hospital refuse. Such refuse consists of a heterogeneous mass of randomly arranged objects which for safety reasons are additionally placed in appropriate containers the purpose of which is to provide at least temporary protection to the person required to handle it within its area of occurrence. Specifically, hospital refuse usually contains infected containers such as syringes, bottles, test tubes, vials and the like which form a protected repository for germs because it is difficult for fluid used for sterilization purposes to reach them. This happens mainly if the infected container is sheltered from the sterilizing fluid by being well within the interior of the mass of refuse. Existing sterilization equipment is not designed for proper effectiveness against a heterogeneous mass of random objects such as hospital refuse, but only against objects arranged non-randomly and in only tendentially limited quantity within the equipment. Even if dimensioned for use for hospital refuse, the effectiveness of such equipment is uncertain, and the sterilization time and capacity for a given overall size and operating cost would certainly vary considerably with the quantity of refuse to be sterilized. Consequently, known equipment would involve much higher times and costs the greater the mass of refuse to be sterilized.

SUMMARY OF THE INVENTION

The object of the present invention is to obviate the aforesaid drawback by providing a sterilization plant able to operate effectively and at tendentially low cost and times on substantial quantities of hospital refuse in the configuration in which it occurs on collection for feeding to disposal.

The shredder eliminates any hollow body which may be present in the refuse and comminutes the refuse so that it can be more easily preheated by the steam injected along the conveyor unit, which being in the form of a screw simultaneously mixes the shredded refuse sufficiently for it to attain an optimum uniform temperature on entry to the oven. When the sterilization chamber (oven) has been filled to its optimum level it is closed and steam is injected to bring the refuse to the required pressure (3 atm) and temperature (min. 132° C.).

Simultaneously, the action of the microwaves results in mass heating to further raise the refuse temperature to above 140° C. and the pressure to between 3 and 3.5 atm. The refuse adhering to the lateral wall of the enclosure also reaches the necessary temperature, which is maintained for the time required for achieving sterilization. In this respect the polytetrafluoroethylene prevents the heat from being transmitted to the walls and consequently ensures that said temperature is reached and maintained for the necessary time.

BRIEF DESCRIPTION OF THE DRAWINGS

The invention is illustrated by way of non-limiting example in the figures of the accompanying drawings.

DETAILED DESCRIPTION

Figure 1:
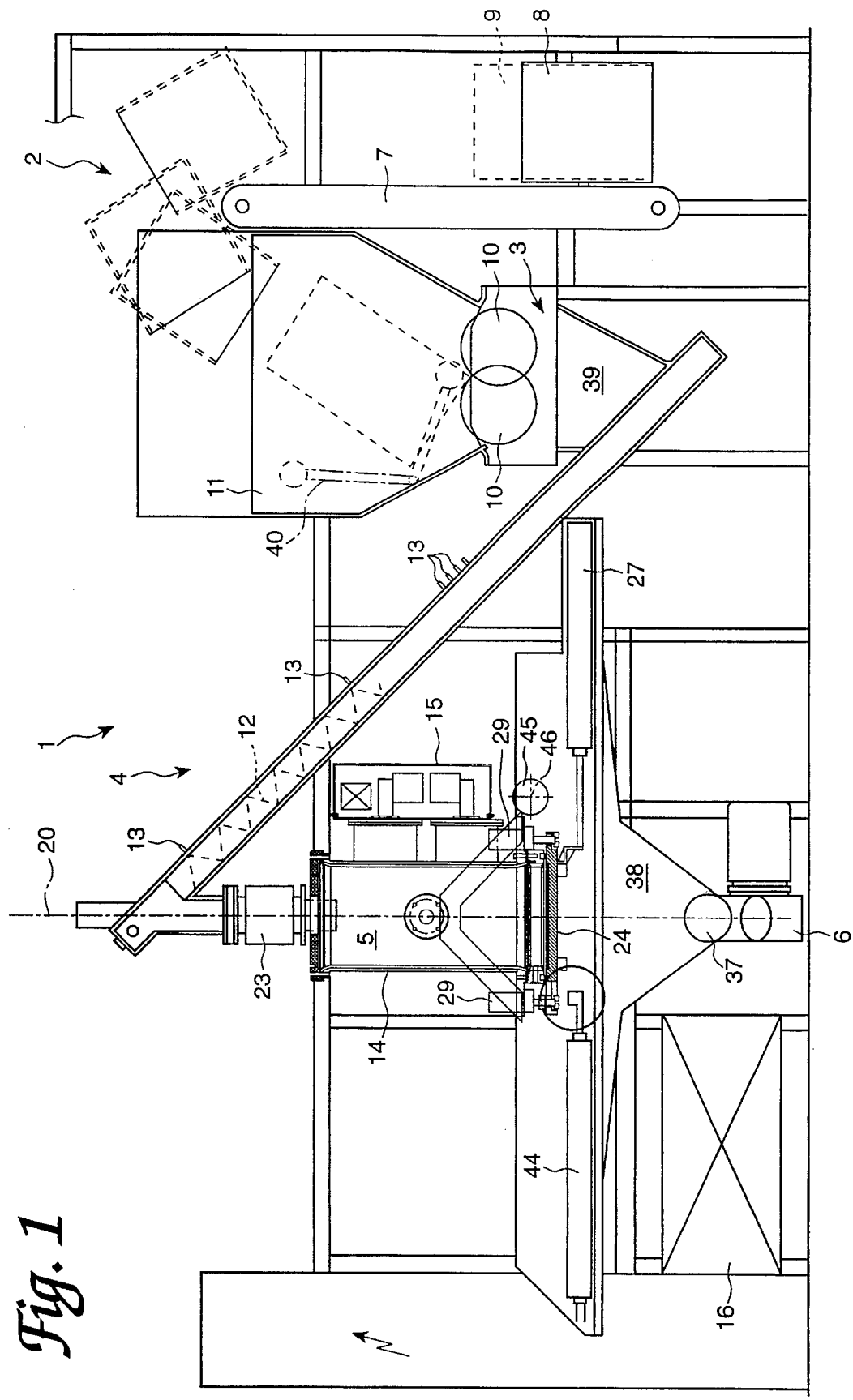
FIG. 1 is a schematic view of a plant according to the invention.
Figure 2:
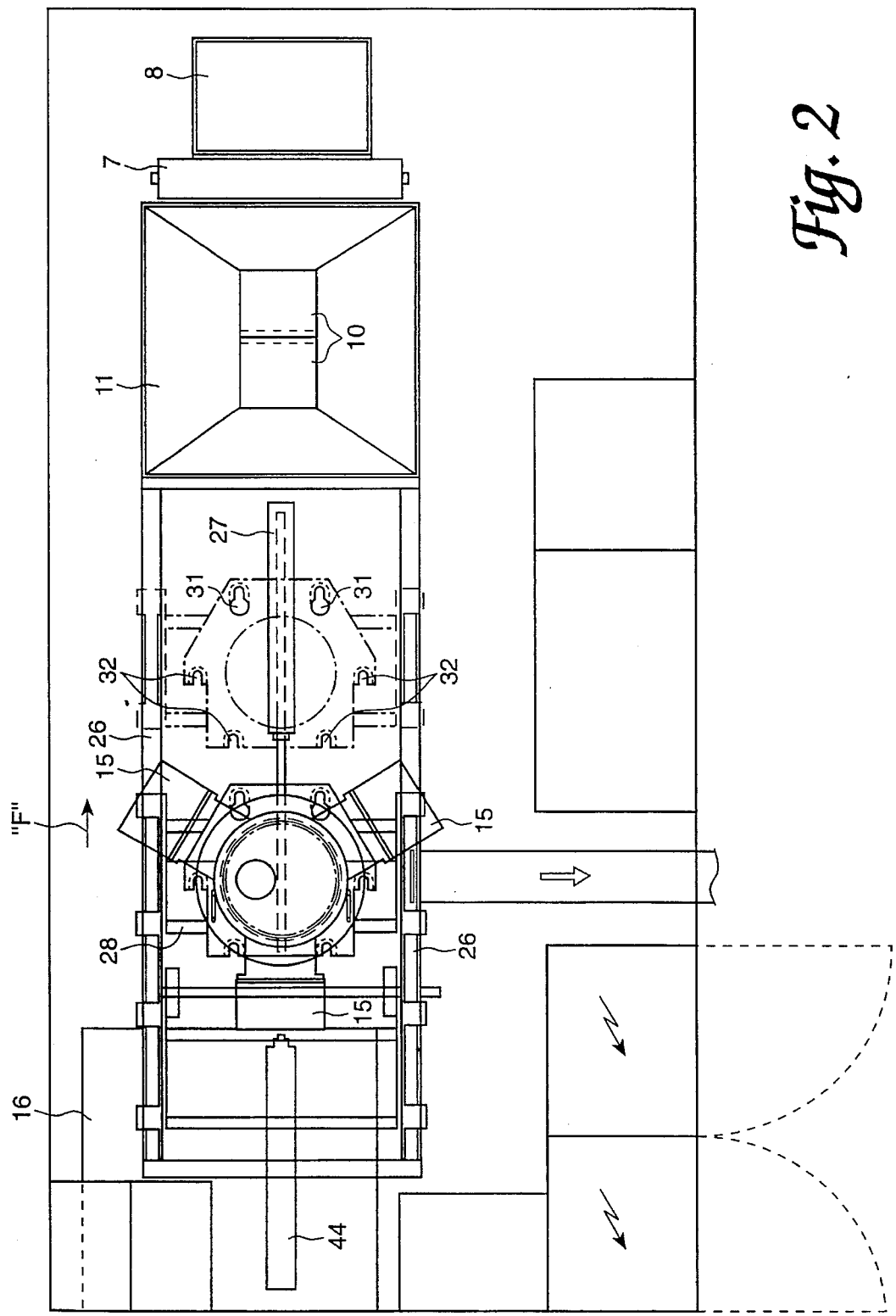
FIG. 2 is a schematic plan view of the plant of FIG. 1.
Figure 3:
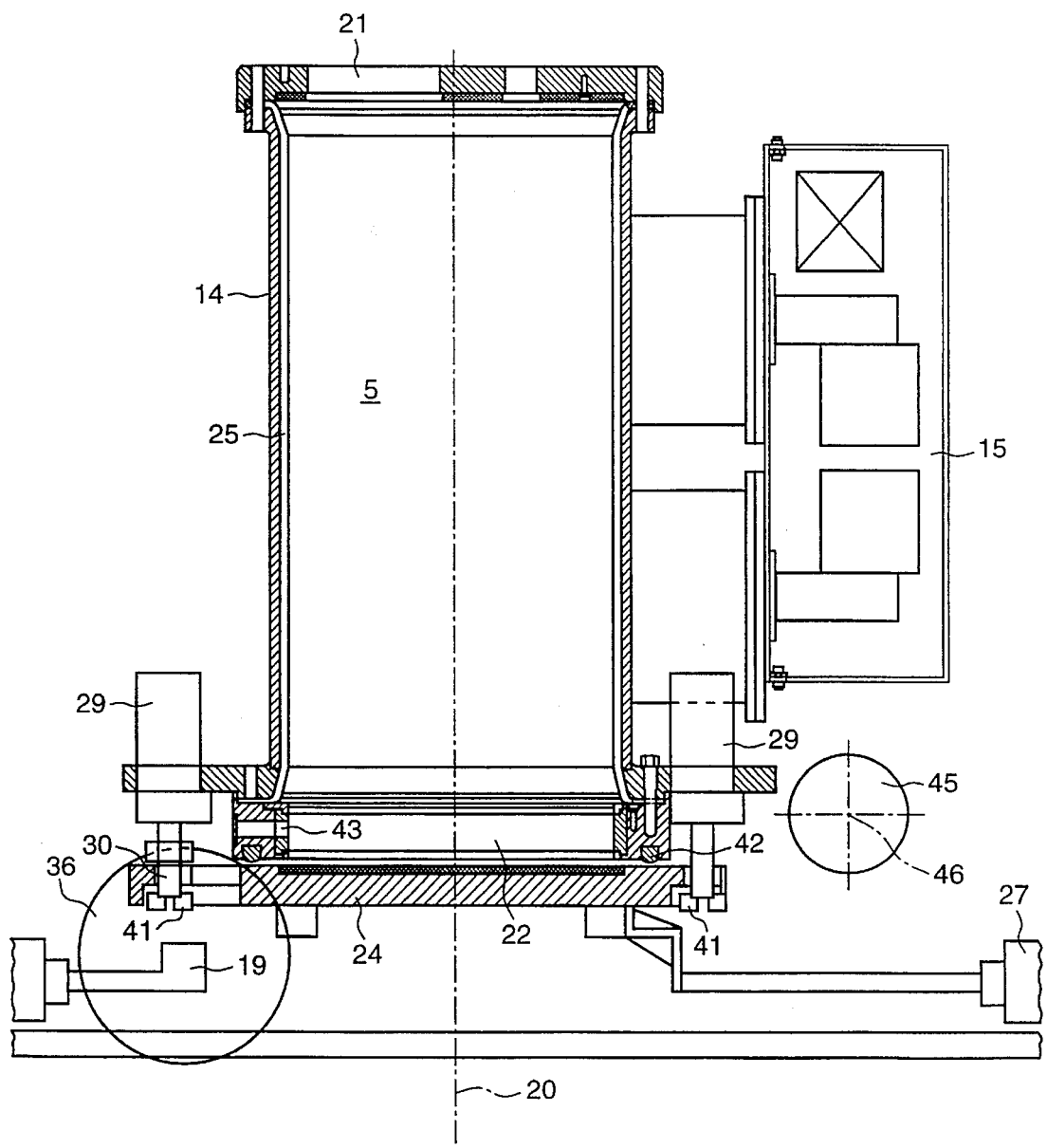
FIG. 3 is a section through the oven.
Figure 4:
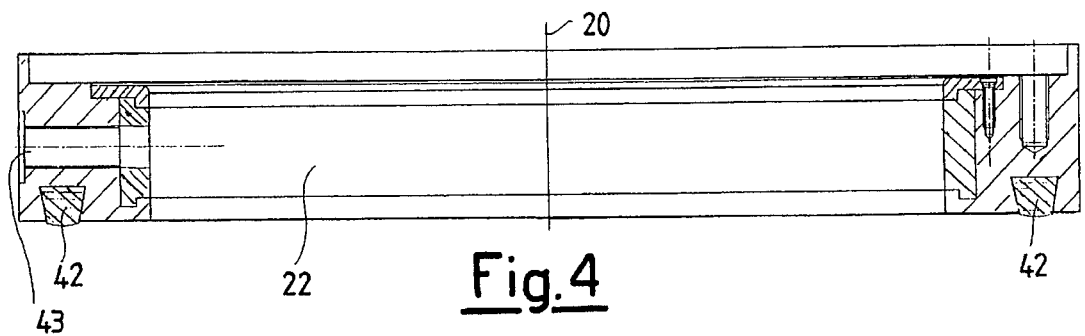
FIG. 4 is a detail of the mouth.
Figure 5:
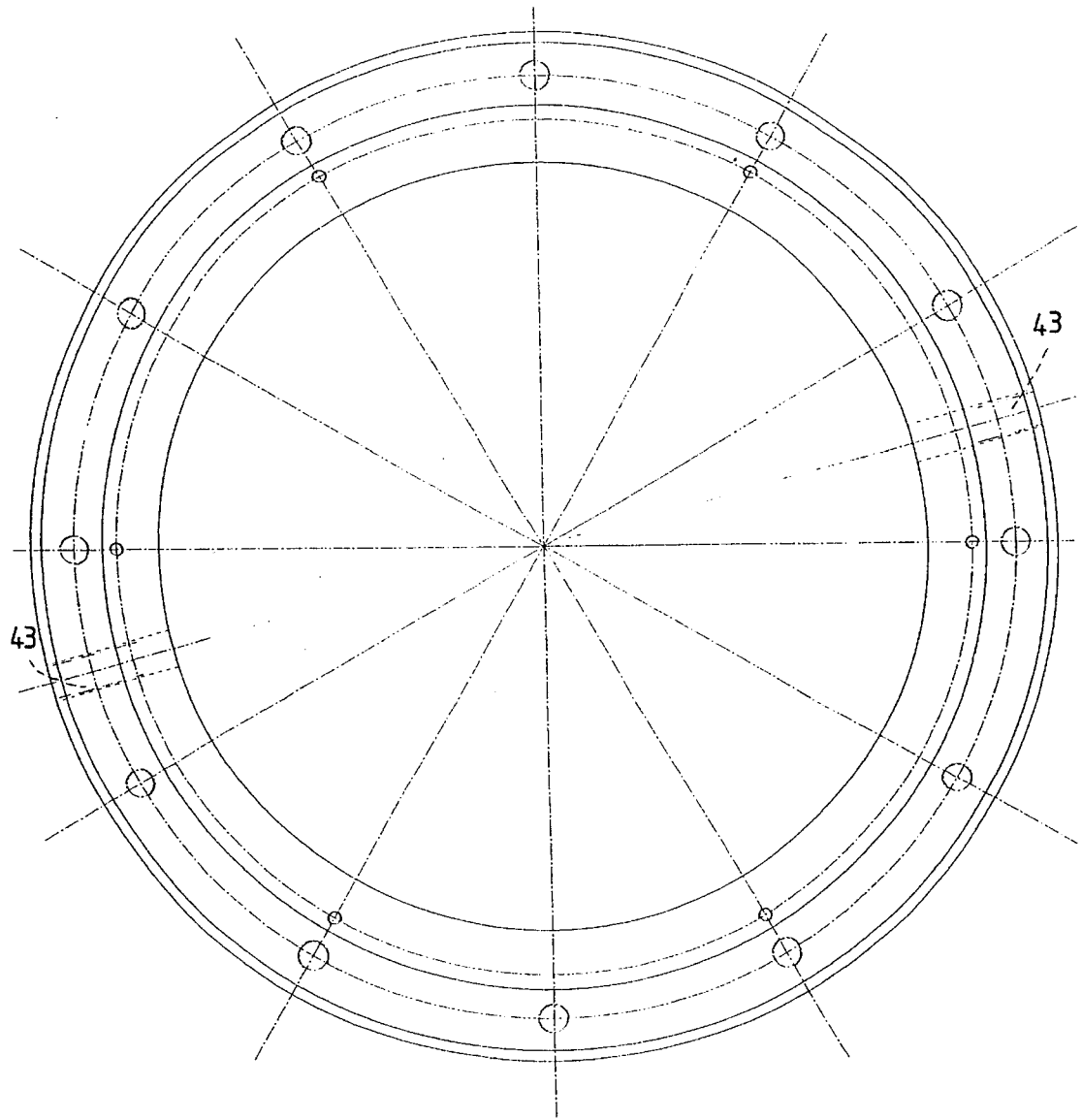
FIG. 5 is a plan view of the detail of FIG. 4.

With reference to the drawing figures, the hospital refuse sterilization plant, indicated overall by 1, comprises a device 2 for loading the refuse into a shredder, a shredder device 3, a conveying and preheating device 4, an oven 5, and a device 6 for removing the treated refuse leaving the oven.

The refuse loading device 2 comprises a chain elevator 7 provided with a container 8 for temporarily holding the containers 9 in which the hospital refuse is placed.

The shredder device 3 is of the type comprising rotary toothed drums 10 and comprises a loading hopper 11 into which the device 2 discharges. Within the hopper 11 there is a pusher device 40 which pushes the received material between the drums 10.

The device 4 for conveying and preheating the hospital refuse comprises a motorized screw 12 along which nozzles 13 are positioned for spraying the preheating fluid.

The oven 5 comprises an enclosure 14, a plurality of microwave generators 15, a steam generating device 16, a device 17 for measuring the extent of filling, a device 18 for the forced expulsion of the refuse and a device 19 for cleaning the oven discharge mouth.

The enclosure 14 is preferably cylindrical and positioned with its axis 20 vertical. It comprises a loading or upper mouth 21 and a discharge or lower mouth 22 which are closed by a ball valve 23 and a sliding cover 24 respectively. The ball valve 23 is connected directly to the upper end of the screw 12.

The enclosure 14 is internally lined with a polytetrafluoroethylene layer 25 the purpose of which is to make the walls insulating and slippery towards any refuse adhering to them. The sliding cover 24 is supported by gravity on a carriage 28 slidable horizontally on guides 26 under the action of a preferably pneumatic cylinder 27. The cover is moved vertically to hermetically seal the lower mouth 22 of the oven by cylinder-piston units 29 arranged circumferentially about the enclosure 14 with their ends 30 engaging in a first series of slots 31 and in a second series of slots 32.

In the illustrated embodiment there are six microwave generators 15 arranged 120° apart on two levels along the circumference of the enclosure 14 to provide maximum efficiency irradiation. During the sterilizing action the microwave generators 15 are aided by the steam generating device 16 which injects the produced steam into the enclosure 14 via ports 43 positioned equidistantly along the perimeter of the discharge mouth 22.

Figure 7:
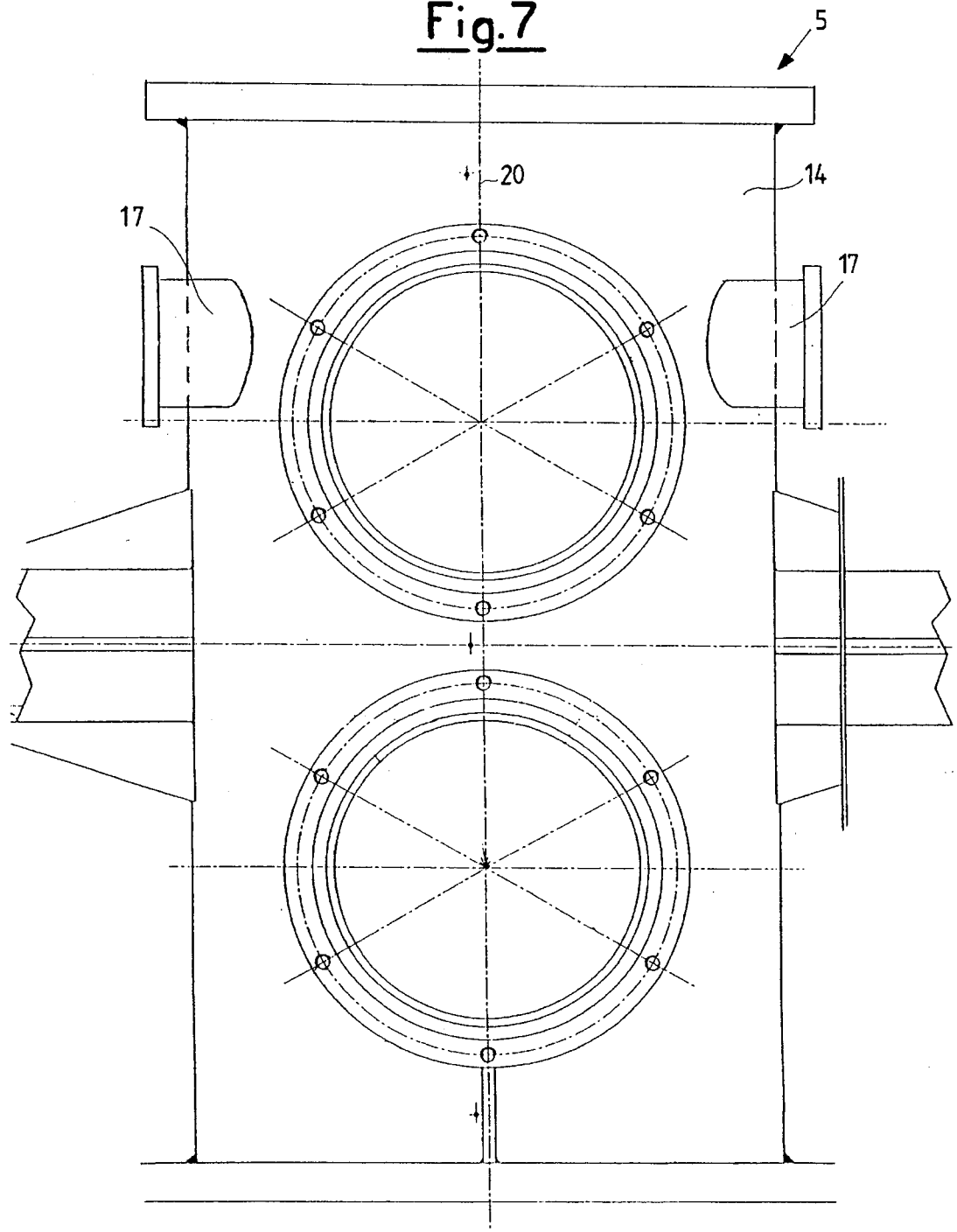
FIG. 7 is a schematic side view of the oven.

The device 17 for measuring the extent of filling can be of optical type or can use a microwave barrier. In the illustrated example it comprises an emitter element with its receiver arranged in a diametrically opposite position (FIG. 7).

Figure 6:
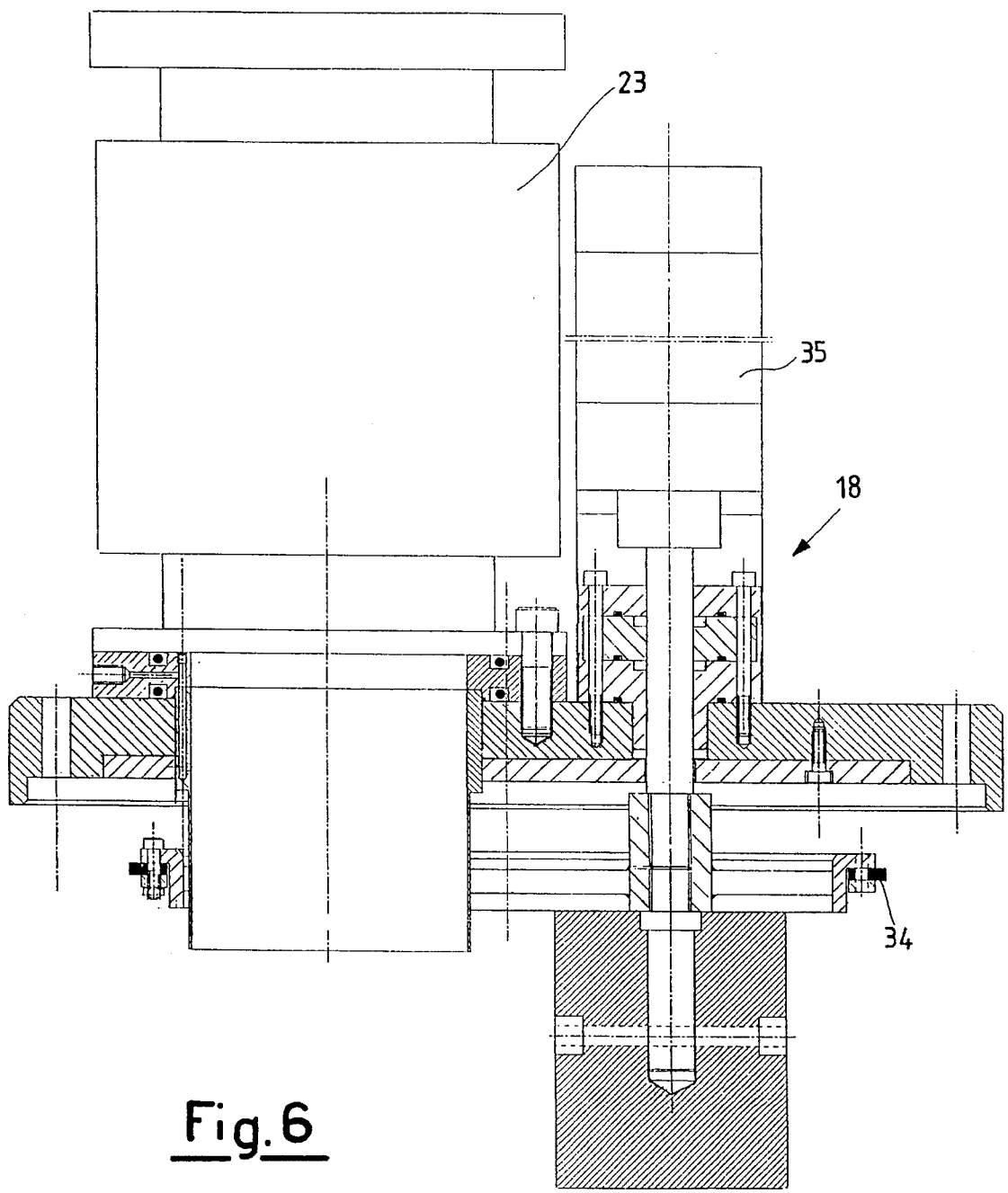
FIG. 6 is a section through the device for compacting the refuse and forcedly expelling it from the oven.

The device 18 for the forced expulsion of the refuse from the enclosure (FIG. 6) comprises an annular brush 34 in contact along its entire length with the inner surface of the enclosure 14 and vertically movable within it by a cylinder 35.

The device 18 is also used for compacting the refuse in order to properly utilize the capacity of the oven. In this case it moves reciprocatingly and cyclically along the axis 20.

The device 19 for cleaning the oven mouth is formed by a brush 36 rotating about itself and simultaneously translating horizontally along the entire width of the discharge or lower mouth 22 by the action of a preferably pneumatic cylinder 44.

The device 6 for removing the treated refuse comprises substantially a motorized screw 37 dipping into a hopper 38. To allow substantially continuous operation of the plant 1 it is provided downstream of the shredder 3 and upstream of the screw 13 with a hopper 39 of adequate volume in which the shredded refuse can be temporarily accumulated while waiting for the oven to be ready to receive it after terminating the treatment under way.

The plant operates as follows.

The hospital refuse contained in its collection and temporary storage containers 9 is placed in the container 8 of the loading device 2, which feeds the container 9 into the shredder 10 where the pusher device 40 feeds the container 9 between the drums 10. The shredded refuse falls into the hopper 39 where it is withdrawn by the motorized screw 12. During its conveying within the screw the refuse is preheated by steam sprayed through the nozzles 13. With the valve 23 open the refuse is fed into the enclosure 14 of the oven 5, where it accumulates by gravity on the base formed by the lower cover 24. The device 18 is periodically operated to reduce the refuse volume. The extent of filling of the oven is checked periodically by the device 17 for measuring the extent of filling. Appropriate devices can be provided so that when the maximum refuse quantity is detected within the oven the operation of the motorized screw 12 and hence the loading of the oven 5 are automatically interrupted and the valve 23 is closed.

Sterilization occurs by the combined action of the microwaves produced by the generators 15 and the steam injected by the device 16 through the ports 43.

The plant is able to sterilize hospital refuse because it is in comminuted form free from hollow pieces and is uniformly moistened so as to be attacked effectively within a short time by the microwaves and by the steam generated by the microwaves and/or injected.

Upon termination of the treatment, after the steam contained in the oven has been recovered and hence the internal pressure is approximately atmospheric, the lower cover 24 is removed. The cylinder-piston units 29 release the cover 24 and deposit it on the carriage 28. The carriage 28 moves in the direction of the arrow F through a distance only sufficient to enable the keys 41 positioned at the outer ends of the piston rods to disengage from both the first series 31 and second series 32 of slots. The rods of the cylinder-piston units 29 can then rise and freely leave the slots 31 and 32, to leave the cover 24 deposited on the carriage 28.

Further movement of the carriage 28 in the direction of the arrow F or in the opposite direction causes the cover 24 to leave the enclosure 14 and enable the now sterilized refuse to fall into the hopper 38, from which the device 6 can remove it. To prevent refuse portions remaining adhering to the inner surface of the enclosure 14, of the lower cover 24 or of the lower discharge mouth 22, the forced expulsion device 18 and the device 19 for cleaning the oven lower mouth are operated. The annular brush 34 of the forced expulsion device 18 moves vertically parallel to the axis 20 to detach from the lateral wall any refuse which has remained attached.

The device 19 for cleaning the oven lower mouth is operated preferably not simultaneously with the forced expulsion device in order not to obstruct the fall into the hopper 38 of any refuse removed from the inner wall of the enclosure 14. The brush 36 simultaneously rotates and translates to clean especially the gasket 42 positioned on the discharge mouth 22 of the enclosure 14. The corresponding contact surfaces on the cover 24 are cleaned by a cylindrical brush 45 rotating about a fixed axis 46 by the effect of the movement of the cover 24 in the direction of the arrow F.

When the refuse has been discharged, the lower discharge mouth 22 is closed and the oven is ready for the next load. The lower cover 24 is positioned below the enclosure 14 so that some of the cylinder-piston units 29 can engage the widest part of the first series 31 of slots while the remainder can descend beyond the second series 32 of slots. A slight subsequent horizontal movement of the cover results in the engagement of the keys 41 of some of the cylinder-piston units 29 with the narrowest portion of the first series 31 of slots and the engagement of the keys 41 of the remaining cylinder-piston units 29 with the remaining slots. By operating all the cylinder-piston units the enclosure 14 is closed in a sealed manner. The oven can then be again loaded.

It is claimed:

1. A hospital refuse sterilization plant for producing treated refuse, comprising in combination the following components, listed in the direction of advancement of hospital refuse within the plant:

a shredder;

a shredded refuse conveying and preheating device formed from a motorized screw along which nozzles are positioned for spraying steam;

an oven formed from an enclosure for the material to be treated, at least one microwave generator, and a device for generating steam and injecting said steam into said enclosure, said enclosure upperly comprising a loading mouth closable by a valve and lowerly comprising a discharge mouth closable by a sliding cover, said enclosure being internally lined with a layer of insulating and antiadherent material, providing an inner surface.

2. A plant as claimed in claim 1, wherein:

said oven is provided with a device for measuring extent of filling of said oven, said measuring device comprising a sensor positioned on the perimeter of said oven.

3. A plant as claimed in claim 1, wherein:

said oven is provided with a device for forced expulsion of refuse, comprising an annular brush in contact with the entire length thereof with said inner surface of said enclosure and movable vertically within said enclosure.

4. A plant as claimed in claim 1, wherein:

said oven is provided with a device for cleaning said discharge mouth, said cleaning device being formed by a brush which rotates while simultaneously translating along the entire width of the said mouth.

5. A plant as claimed in claim 1, further comprising:

a device for removing said treated refuse leaving said oven.

6. A plant as claimed in claim 5, wherein:

said refuse removal device comprises a motorized screw.

7. A plant as claimed in claim 1, wherein:

said shredder comprises rotating toothed drums.

8. A plant as claimed in claim 1, wherein:

said layer of insulating and antiadherent material is made of polytetrafluoroethylene.

9. A plant as claimed in claim 1, wherein:

said oven comprises a plurality of said microwave generators arranged on two levels equidistantly about the perimeter of said enclosure.

10. A plant as claimed in claim 9, wherein:

said steam generating device produces said steam at a temperature of 160° C.

11. A plant as claimed in claim 1, wherein:

said steam generating device is arranged to inject said steam via equidistant ports positioned at said discharge mouth of said oven.

12. A plant as claimed in claim 1, wherein:

said cover for closing said discharge mouth is arranged to translate horizontally relative to said mouth by virtue of horizontal guides and cylinders interposed between said cover and said guides, and said cover is arranged to be applied in a sealed manner to said discharge mouth by a plurality of vertically acting cylinder-piston units engaging slots provided in said cover.

13. A plant as claimed in claim 1, wherein:

a chamber for temporary accumulation of the shredded refuse is provided between said shredder and said refuse conveying and preheating device.

14. A plant as claimed in claim 1, further comprising:

a device for loading refuse into the shredder.

15. A plant as claimed in claim 14, wherein:

said device for loading refuse into said shredder comprises a chain elevator provided with a container for temporarily housing containers containing said hospital refuse.

* * * * *